United States Patent [19]

Perlin

[11] 4,407,285
[45] Oct. 4, 1983

[54] MICROSURGICAL CLIP FOR BRAIN SURGERY OR THE LIKE

[75] Inventor: Afred R. Perlin, Highland Park, Ill.

[73] Assignee: Metatech Corporation, Northbrook, Ill.

[21] Appl. No.: 253,191

[22] Filed: Apr. 13, 1981

[51] Int. Cl.³ .............................................. A61B 17/12
[52] U.S. Cl. .................................... 128/325; 128/346; 24/252 R
[58] Field of Search ............... 128/325, 326, 346, 321, 128/354; 251/9, 10; 24/255 R, 248 R, 252 R; D24/27; 81/43

[56] References Cited

U.S. PATENT DOCUMENTS 3,175,263  3/1965  Bernstein ............................ 128/346
3,911,926  10/1975  Peters ............................... 128/346 X

FOREIGN PATENT DOCUMENTS 987375  8/1951  France .............................. 24/252 R Primary Examiner—Michael H. Thaler
Attorney, Agent, or Firm—Leydig, Voit, Osann, Mayer & Holt, Ltd.

[57] ABSTRACT

A microsurgical clip for clamping of small blood vessels formed of a hollow shell of generally rectangular shape having opposed side walls and a front wall, the shell having a duck bill, or jaw, extending forwardly at the lower edge of the front wall. A cooperating insert of zigzag shape nested in the shell includes a top wall, front wall and duck bill, the insert being hinged between the side walls. An expansible spring is seated between the bottom wall of the shell and the top wall of the insert for biasing the duck bills into resilient clamping engagement. The hinge connection includes a hinge pin extending between the side walls at the upper back corners encircled by a tab bent at the end of the top wall of the insert. The side walls are angled downwardly from the hinge pin and the front wall of the shell is foreshortened so that when the duck bills are in clamping engagement the insert projects upwardly beyond the shell. When the projecting insert is pinched downwardly by the finger tip the spring is compressed accompanied by relative spreading of the duck bills for engagement of a blood vessel therebetween. It is one of the features of the construction that the back of the shell is open to provide a spring access opening for insertion of a selected spring to produce a predetermined degree of clamping force.

6 Claims, 6 Drawing Figures

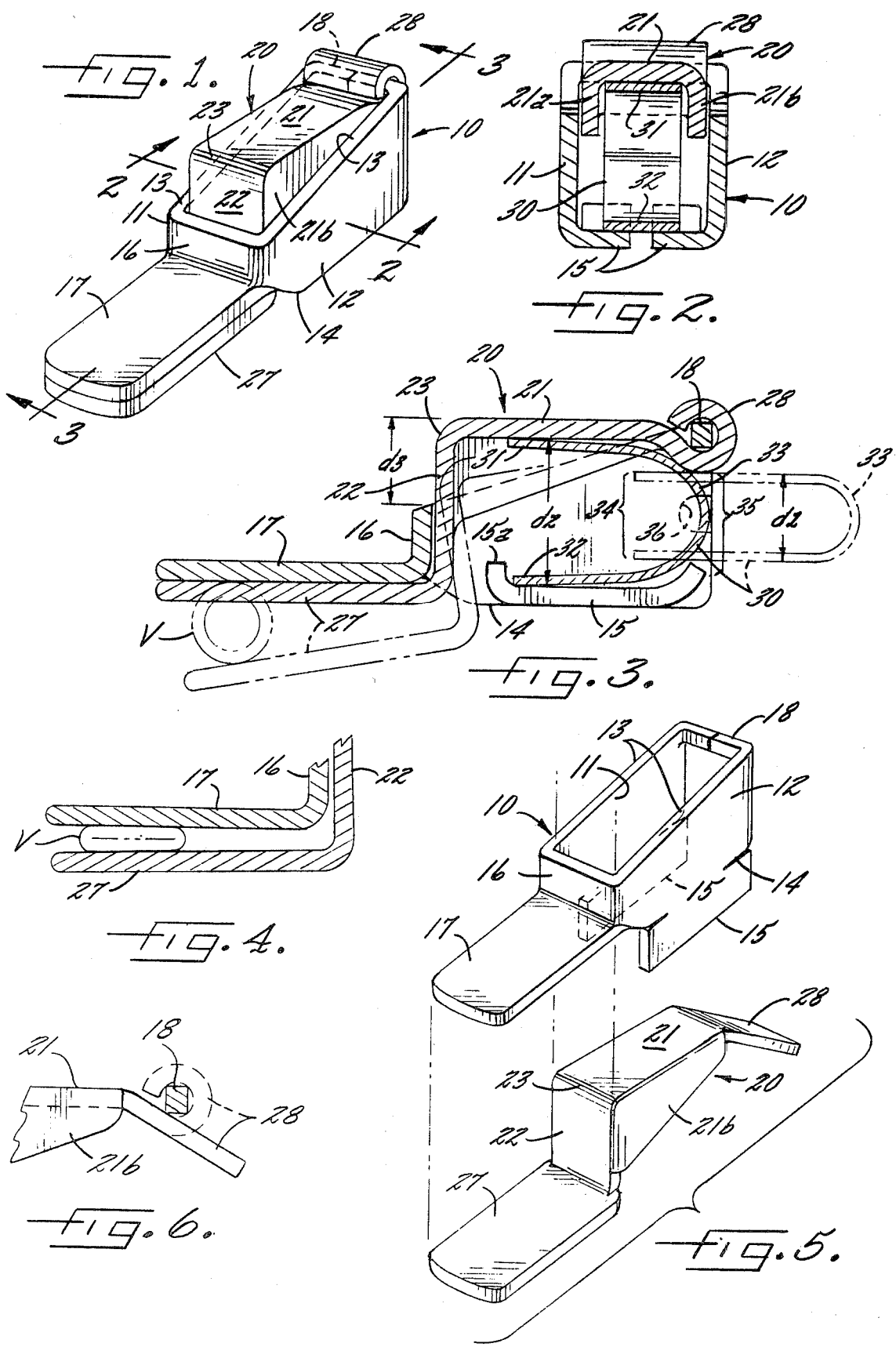

MICROSURGICAL CLIP FOR BRAIN SURGERY OR THE LIKE

In doing surgery on parts of the body which are supplied by numerous small blood vessels it is necessary to clamp off the blood vessels individually in order to reduce the amount of blood discharged into the field. The clamps which have been available for this purpose in the past have been of unwieldy construction applying pressure which is highly localized, usually excessive, and largely unpredictable so that blood vessels are often crushed or otherwise irreparably damaged. Nevertheless such clamps particularly those intended for specialized purposes such as brain surgery, have been extremely expensive.

In my copending application Ser. No. 154,613 which was filed May 30, 1980, now U.S. Pat. No. 4,324,248 there is disclosed a miniaturized clamp having a shell and cooperating insert molded of plastic integrally with one another with a live hinge interconnecting the two parts.

It is a main object of the invention to provide a microsurgical clip processing features and advantages which are similar to those discussed in the above copending application but which is differently constructed, with a free hinge, and which is intended to be made of metal rather than plastic.

Thus it is an object of the present invention to provide a microsurgical clip for clamping of small blood vessels which will not crush or otherwise injure even the most fragile of vessels. It is a related object to provide a microsurgical clip in which the clamping force may be precisely determined by precalibration of the metal spring which exerts the clamping force.

It is a more specific object in this connection to provide a microsurgical clip which is of uniform construction but which may be fitted with springs in increments of stiffness and identified, if desired, by color coding, so that the clamping force may be tailored to the type and size of blood vessel being clamped.

It is a further object of the invention to provide a microsurgical clip which consists of a metal shell and metal insert plus a spring all secured captively and intimately together so that there is no possibility of losing a part of the clip in the wound. Thus it is an object to provide a clip which can be used with confidence and which, notwithstanding its small size, is easily grasped and operated with light pinching pressure, with no risk of overstressing the spring.

It is one of the important objects of the present invention to provide a microsurgical clip which is highly economical, which can be easily and cheaply fabricated using quantity production techniques and in which the spring which provides the clamping force may be quickly and easily inserted into secure operating position, if desired, just before use. Because of its economy the clip may be discarded after use or readily sterilized for re-use.

Other objects and advantages of the invention will become apparent upon reading the attached detailed description and reference to the drawings in which:

FIG. 1 is a perspective view showing a microsurgical clip constructed in accordance with the invention.

FIG. 2 is a transverse section taken along line 2—2 in FIG. 1.

FIG. 3 is a longitudinal section taken along line 3—3 in FIG. 1.

FIG. 4 is a fragmentary side profile showing the clamping of a blood vessel.

FIG. 5 is an exploded view of the shell and insert prior to being assembled together.

FIG. 6 is a fragmentary view showing the nature of the hinge connection between the parts.

While the invention has been described in connection with a preferred embodiment, it will be understood that I do not intend to be limited to the particular embodiment shown but intend, on the contrary, to cover the various alternative and equivalent constructions included within the spirit and scope of the appended claims.

Turning now to the drawings there is shown a miniaturized clip, referred to herein as a microsurgical clip, constructed in accordance with the invention and formed of a hollow shell or housing 10 having opposed side walls 11, 12 each of which has an upper edge 13 and a lower edge 14. Integrally connected to the lower edges is a bottom wall consisting of sections 15 in the form of inwardly bent tabs. Extending between the side walls is a front wall 16, and projecting forwardly at the lower edge of the front wall, and integral therewith, is a duck bill 17. Spanning the side walls 11, 12 in a position adjacent the back of the shell is a hinge pin 18 to which more detailed reference will be made.

A cooperating insert of zigzag shape is nested in the shell. Such insert, indicated at 20, is made up of a top wall 21, a front wall 22 generally perpendicular thereto, forming a corner 23, and an integral duck bill 27 projecting forwardly from the front wall. As will be noted in FIG. 3, the bottom wall 15 of the shell is foreshortened to provide a downwardly facing aperture immediately behind the front wall 16 of the shell, the front wall of the insert being vertically dimensioned to extend downwardly through the aperture in the bottom wall so that the duck bill on the insert flatly and comformingly underlies the duck bill on the shell. The top wall 21 of the insert terminates in a tab 28 which is bent to freely and substantially completely encircle the hinge pin 18 thereby keeping the shell and insert captive with respect to one another so that they cannot possibly become separated in the wound.

For the purpose of biasing the duck bills into resilient clamping engagement with one another an expansible spring 30 is seated between the bottom wall 15 of the shell and the top wall 21 of the insert. Such spring is preferably in the form of a leaf spring of "C" configuration having opposed legs 31, 32, a closed end 33 and an open end 34 the open side of the "C" facing forwardly within the clip.

In accordance with one of the aspects of the invention the back of the shell is preferably open to provide a spring access opening 35 having a horizontal dimension greater than the width of the spring and a vertical dimension d1 which is large enough to receive the spring in the compressed state but which is less than the head room d2 within the clip when in its clamping state, thereby causing the spring to be securely retained once it is inserted.

In carrying out the invention the insert 20 is relatively formed with respect to the shell so that it projects upwardly above the side walls of the shell and through the open top thereof so that application of pinching pressure by the finger tip, in the manner of pinching a clothes pin, causes the projecting insert to move downwardly with respect to the shell, compressing the spring and accompanied by relative spreading of the duck bills for engagement of a blood vessel V.

In accordance with one of the more specific aspects of the present invention the upper edges 13 of the side walls 11, 12 of the shell are angularly relieved, and the front wall 22 is correspondingly foreshortened, thereby to expose, and provide access to the corner 23 of the insert which projects relatively upwardly. The "depth" of the relief is indicated at d3 in FIG. 3. In the preferred, illustrated, construction the hinge pin 18 extends between the upper back corners of the side walls, integral with at least one of them, and the upper edges 13 of the side walls have a uniform downward slope, which may be at an angle on the order of 20 degrees or more, terminating at the upper edge of the front wall 16. Hingeing the members together at a high level has the advantage that there is no risk of interference between the front wall 22 of the insert and the front wall 16 of the shell as the insert swings downwardly to spread the jaws.

Because the clip is so highly miniaturized the spacing between the side walls 11, 12 is only a small fraction of the width of a fingertip. The upper edges 13 of the side walls are thus bridged by the fingertip and serve as stop surfaces beyond which the insert cannot be pressed. Thus the limited depth d3 of the relief limits the spread of the jaws and insures that the spring 30 is operated well within its elastic limit.

By providing the spring access opening 35 in the back of the clip under the hinge pin it is possible to insert a spring of selected strength after the clip has been assembled and, indeed, just before the clip is to be used. Thus clips may be furnished to the operating facility in the "hollow" state, without springs, and may be accompanied by loose springs having the same geometry but of different strengths with the strength being identified, if desired, by color coding.

To make a clip operative a spring 30 may be compressed between the finger tips and slipped into spring access opening 35. Upon being fully inserted the spring snaps into a secure seated position so that there is no danger that the spring might become separated and lost in the wound.

If desired the clip may be constructed to provide access to the closed end 33 of the spring so that it may be retrieved simply by hooking, the spring being free of positive attachment to either the shell or to the insert. Such access may be provided by forming a notch, shown at 36 in dot-dash outline, in one or both of the side walls 11, 12.

For the purpose of providing a more well-defined "seat" for the upper leg 31 of the spring, to reinforce the insert, and to give the clip a more "enclosed" appearance in the assembled state, the top wall 21 of the insert is preferably formed with integral downwardly extending side skirts indicated at 21a, 21b.

It will be apparent to one skilled in the art that the three parts of which the clip is composed are simply and cheaply formed and easily and quickly assembled together. Referring to FIG. 5 the insert is first nested in the shell into a "bottomed" position (FIG. 3) in which the duck bills are in flatly opposed cooperating relation. The tab 28 at the back end of the insert is then bent around the hinge pin 18 as shown in FIG. 6, using an appropriate bending tool. The tabs which, together, form the bottom 15 of the shell are then bent inwardly from the straight position illustrated in FIG. 5 to the inwardly bent condition illustrated in FIG. 2, thus completing assembly of the shell and insert. In such condition the parts are loosely pivoted together free of any binding which might affect the clamping force. As a final step the spring 30 is squeezed together applying fingertip pressure and inserted through the open back end 35 of the clip. Upon full insertion the legs of the springs snap outwardly from one another thereby locking the spring in its seated position. To form a limit stop for the spring the front edge of the bottom members 15 may be turned upwardly as indicated at 15a in FIG. 3. Alternatively the upper leg 31 of the spring may be elongated to the extent that when the spring is in seated position the upper leg engages the front wall 22 of the insert.

The illustrated embodiment includes a bottom closure 15 which is rather extensive. It will be understood that the purpose of the bottom is not to provide complete closure but simply to provide a member against which the lower leg 32 of the spring may react. Accordingly, the bottom may be reduced in area from that shown and may, as a limit condition, consist simply of a narrow cross piece supporting the lower leg of the spring.

It will be apparent that the clip described above meets all of the earlier stated objects of the invention. Because of the complete freedom of movement between the parts of the clip it can be calibrated for application of a consistent force. Or if desired a set of springs may be separately supplied calibrated to different force levels for insertion at the place of use. In any event, the clamping force is accurately predetermined and limited so that the clip will not crush or otherwise injure even the most fragile of vessels.

The clip is durably made of metal which facilitates sterilization and re-use. The clip is easily manipulated by the finger tip and there is no possibility of overstressing the spring in temporarily releasing the clamping force for engagement of a blood vessel which might affect the calibration. Finally, the clip is of simple and highly economical construction easily assembled and highly reliable notwithtanding its extremely small size. Indeed it is found that clips of this design may be successfully made and used in which the maximum dimension is less than a centimeter.

While a single spring has been illustrated in the drawing, it will be understood that the term "spring" includes the possibility of using a multiple, or laminated, spring, with one additional laminate to be added for each increment of force which is desired, thereby accommodating the same basic clip structure to a multiplicity of blood vessel sizes.

What I claim is:

1. A microsurgical clip for clamping of small blood vessels comprising, in combination, a hollow shell or generally rectangular shape having (a) opposed side walls, (b) a bottom wall and (c) a front wall, the back and top of the shell being open, the shell having (d) a duck bill projecting forwardly at lower edge of the front wall and integral therewith, a cooperating insert of zigzag shape nested in the shell and made up of (1) a top wall, (2) a front wall generally perpendicular thereto and (3) an integral duck bill projecting forwardly at the lower edge of its front wall, the bottom wall being foreshortened to provide a downwardly facing aperture immediately behind the front wall of the shell, the front wall of the insert being vertically dimensioned to extend downwardly through the aperture in the bottom wall so that the duck bill on the insert flatly and conformingly underlies the duck bill on the shell, the insert having its top wall captively hinged between the side walls in a position adjacent the back of the shell, and an expensible spring seated between the bottom wall of the shell and the top wall of the insert for urging the insert relatively upwardly in the shell thereby biasing the duck bills into resilient clamping engagement with one another, the upper edges of the side walls being angled downwardly from the back toward the front wall, the side walls and the front wall of the shell being relieved by making them of reduced height so that the insert is exposed with the forward portion thereof projecting upwardly from the shell with the result that fingertip application of pinching pressure to the projecting insert causes it to move downwardly with respect to the shell compressing the spring and accompanied by relative spreading of the duck bills for engagement of a blood vessel therebetween, the spacing between the side wall being only a small fraction of the width of a fingertip, and the depth of the relief, and hence the range of spreading movement, being limited to insure that the spring is operated well within its elastic limit.

2. A microsurgical clip for clamping of small blood vessels comprising, in combination, a hollow shell of generally rectangular shape having (a) opposed side walls having upper back corners, (b) a bottom wall and (c) a front wall, the top of the shell being open, the shell having (d) a duck bill projecting forwardly at lower edge of the front wall and integral therewith, a cooperating insert of zigzag shape nested in the shell and made up of (1) a top wall, (2) a front wall generally perpendicular thereto to form a corner and (3) an integral duck bill projecting forwardly at the lower edge of its front wall, the bottom wall being foreshortened to provide a downwardly facing aperture immediately behind the front wall of the shell, the front wall of the insert being vertically dimensioned to extend downwardly through the aperture in the bottom wall so that the duck bill on the insert flatly and conformingly underlies the duck bill on the shell, a hinge connection for hinging the top wall of the insert between the side walls in a position adjacent the back of the shell, and an expansible spring seated between the bottom wall of the shell and the top wall of the insert for urging the insert relatively upwardly in the shell thereby biasing the duck bills into resilient clamping engagement with one another, the hinge connection including a hinge pin extending between the side walls at the upper back corners thereof, the hinge pin being substantially completely encircled by a tab formed at the end of the top wall of the insert so that the shell and insert are permanently captive to one another, the side walls of the shell being angled downwardly from the hinge pin and the front wall being foreshortened so that when the duck bills are in clamping engagement the corner on the insert projects upwardly beyond the shell so that fingertip application of pinching pressure to the projecting insert causes it to move downwardly with respect to the shell compressing the spring and accompanied by relative spreading of the duck bills for engagement of a blood vessel therebetween.

3. The combination as claimed in claim 2 or in claim 1 in which the open back provides a spring access opening having a horizontal dimension greater than the width of the spring and a vertical dimension which is large enough to insert the spring in the compressed state but less than the head room within the clip when in its clamping state thereby causing the spring to be securely retained while free of positive attachment to either the shell or insert, the spring being a leaf spring of "C" configuration with the open side of the "C" facing forwardly within the clip.

4. The combination as claimed in claim 1 or in claim 2 in which the top wall of the insert is formed with integral downwardly extending side skirts for enclosing the space thereunder.

5. The combination as claimed in claim 1 or in claim 2 in which the bottom wall comprises an inwardly bent tab integrally formed on the bottom edge of at least one of the side walls.

6. The combination as claimed in claim 2 in which the hinge pin is integral with at least one of the side walls of the shell and extends at right angles thereto.

* * * * *

UNITED STATES PATENT AND TRADEMARK OFFICE
CERTIFICATE OF CORRECTION

PATENT NO. : 4,407,285
DATED : October 4, 1983
INVENTOR(S) : Alfred R. Perlin

It is certified that error appears in the above-identified patent and that said Letters Patent is hereby corrected as shown below:

On the title page

Name of Inventor: replace "Afred" with -Alfred-

Line 24, Column 1: replace "processing" with -possessing-

Signed and Sealed this

Thirty-first Day of January 1984

[SEAL]

Attest:

Attesting Officer

GERALD J. MOSSINGHOFF

Commissioner of Patents and Trademarks